United States Patent
Burlutskaya et al.

(10) Patent No.: US 9,878,067 B2
(45) Date of Patent: Jan. 30, 2018

(54) HISTO-EQUIVALENT BIOPLASTIC MATERIAL

(71) Applicant: G-Group LLC, St. Petersburg (RU)

(72) Inventors: Olga Ivanovna Burlutskaya, Orenburg (RU); Ramil Rafailevich Rakhmatullin, Orenburg (RU); Tatyana Ivanovna Burtseva, Orenburg (RU); Abay Izhbulatovich Adelshin, Sagarchin (RU)

(73) Assignee: G-Group LLC, St. Petersburg (RU)

( * ) Notice: Subject to any disclaimer, the term of this patent is extended or adjusted under 35 U.S.C. 154(b) by 211 days.

(21) Appl. No.: 14/442,209

(22) PCT Filed: Sep. 12, 2013

(86) PCT No.: PCT/RU2013/000795
§ 371 (c)(1),
(2) Date: May 12, 2015

(87) PCT Pub. No.: WO2014/129929
PCT Pub. Date: Aug. 28, 2014

(65) Prior Publication Data
US 2016/0256603 A1    Sep. 8, 2016

(30) Foreign Application Priority Data

Feb. 21, 2013   (RU) ................................ 2013107843

(51) Int. Cl.
*A61L 27/20*   (2006.01)
*A61L 2/22*    (2006.01)
(Continued)

(52) U.S. Cl.
CPC .............. *A61L 27/20* (2013.01); *A61L 26/008* (2013.01); *A61L 26/0023* (2013.01); *A61L 27/22* (2013.01)

(58) Field of Classification Search
CPC ........... A61F 2/10; A61F 2/105; A61F 2/0063
(Continued)

(56) References Cited

U.S. PATENT DOCUMENTS

| 7,217,853 B2 * | 5/2007 | Kulichikhin .......... A61L 15/585 |
| | | 106/205.01 |
| 8,697,656 B2 * | 4/2014 | Fournial .................. A61K 8/64 |
| | | 514/18.6 |

(Continued)

FOREIGN PATENT DOCUMENTS

| RU | 2 425 694 C1 | 8/2011 |
| RU | 2 438 648 C1 | 1/2012 |

OTHER PUBLICATIONS

"Bioartifical Organs" by Claudy Mullon. E-Biomed vol. 1-2000. pp. 43-45 Apr. 13, 2000.
(Continued)

*Primary Examiner* — Suzette J Gherbi
(74) *Attorney, Agent, or Firm* — McCormick, Paulding & Huber LLP

(57) ABSTRACT

The invention relates to medicine and specifically to combustiology, to surgery, and to cosmetology and can be used as a bioplastic material for replacing defects in epithelial tissues (protecting against evaporation and infection) and for stimulating regeneration. The technical result is increased efficacy in healing wounds. The goal is achieved in that a histo-equivalent bioplastic material is used which includes a substrate in the form of a matrix, the material for which is a native form of hyaluronic acid, distinguished in that the histo-equivalent bioplastic material contains a 1.5% solution of hyaluronic acid and a 5% solution of a peptide complex which are mixed until a viscous elastic gel is formed, situated in the foundation and subjected to ultraviolet photopolymerization in a biosafety cabinet over the course of 5-7 hours at the following quantitative ratio in ml: 1.5%
(Continued)

solution of hyaluronic acid solution: 80-90%; 5% solution of peptide complex: 10-20%; the finished material has perforations and notches.

5 Claims, 6 Drawing Sheets

(51) Int. Cl.
*A61F 2/10* (2006.01)
*A61L 26/00* (2006.01)
*A61L 27/22* (2006.01)

(58) Field of Classification Search
USPC ................................ 623/15.11–15.12, 23.72
See application file for complete search history.

(56) References Cited

U.S. PATENT DOCUMENTS

| | | | | |
|---|---|---|---|---|
| 2006/0246113 | A1* | 11/2006 | Griffith | A61F 2/10 424/427 |
| 2010/0291058 | A1* | 11/2010 | Bowlin | A61K 38/363 424/94.5 |
| 2015/0071871 | A1* | 3/2015 | Griffith | A61F 2/10 424/78.22 |
| 2015/0202304 | A1* | 7/2015 | Kaplan | A61K 8/64 424/401 |

OTHER PUBLICATIONS

"Synthesis, Structure and Properties of Polyhydroxyalkanoates: Biological Polyesters" by K. Sudesh, et al. Progress in Polymer Science. Elsevier Science Ltd. Japan pp. 1503-1555. Jul. 27, 2000.

"Biosynthesis and Characterization of Polyhydroxyalkanoate Blends Accumulated by Pseudomonas sp. USM 4-55" by Kumar Sudesh, et al. School of Biological Sciences and National Poison Center. Malaysia. pp. 1-18.

"Biopolymers for Medical and Pharmaceutical Applications: Humic Substances, Polyisoprenoids, Polyesters, and Polysaccharides" by Alexander Steinbuchel and Robert H. Marchessault. Wiley-Blackwell. Jun. 2005. pp. 123-132.

"Evaluation of Metallic and Polymeric Biomaterial Surface Energy and Surface Roughness Characteristics for Directed Cell Adhesion" by Nadim J. Hallab, et al. Tissue Engineering vol. 7, No. 1, 2001. pp. 55-71.

"Biocompatibilty", edited by Sevastyanov V. I., Moscow, 1999; pp. 11-12, and English Translation of the introduction.

"Xenotransplantation: Scientific and Ethic Problems" by V.I. Shumakov, A.G. Tonevitskiy; Human, 1999, No. 6; and English Translation of the first three paragraphs.

"Polymers for medical biological application" by Shtilman M.I., , M: IKC Academkniga, 2006; chapter 5, par. 5.2.2, p. 182 and its English Translation.

"Materials for Medicine, Cell and Tissue Engineering," by Volova T.G., Krasnoyarsk: IPK SFU, 2009; and English Translation of p. 18, last paragraph to p. 19, 2nd paragraph.

"Biocompatible and Functional Properties of Hybrid Composite of Polyhydroxybutyrate/Hydroxyapatite:,Letters of Transplantology and Artificial Organs", by Shishatskaya E.I. 2006, No. 3, pp. 34-38; and English Translation of the Introduction.

"Questions of Cell Technology and Tissue Bioengineering (Review)", by Khlyusov I.A. SFU Journal, 2008, vol. 1, No. 3, pp. 269-294; and English translation of excerpts from pp. 274-275.

"Bioplastic Material Based on Hyaluronic Acid: Biophysical Aspects of Pharmacological Properties", by Rakhmatullin R. R. Journal of Pharmacy, 2011, No. 4, pp. 37-39; and English translations of excerpts from pp. 38-39.

"Efficacy of New Method for Regeneration of Skin Defect in a Patient Suffering from Epidermolysis Bullosa: A Clinical Observation". by Rakhmatullin R.R., Burlutskaya O.I., Adelshina L.R., Burtseva T.I. Current pediatrics, 2011, vol. 10, No. 2, pp. 190-192; and Enclosed English abstract found in fig. 3 on p. 39.

"On the Contact of Elastic Solids." by Hertz H; Pure and Applied Mathematics Journal, 1881, 92:156-171; and English Translation 1st and 2nd paragraphs.

English Translation of Katalog "Professionalnaya kosmetika" TETe Cosmeceutical, Gialuronovaia Kislota + kompleks peptidove 30 ml (3x10ml), Oct. 11, 2012. (2 pages).

International Search Report for Serial No. PCT/RU2013/000795 dated Feb. 6, 2014.

* cited by examiner

HISTO-EQUIVALENT BIOPLASTIC MATERIAL

CROSS-REFERENCE TO RELATED APPLICATION

This application is entitled to the benefit of and incorporates by reference subject matter disclosed in International Patent Application No. PCT/RU2013/000795 filed on Sep. 12, 2013 and Russian Patent Application 2013107843 filed Feb. 21, 2013.

TECHNICAL FIELD

The invention relates to medicine, namely to combustiology, surgery, cosmetology, and may find use as a bioplastic material for replacement of defects in epithelium tissues (protection from evaporation and infection) and stimulation of regeneration.

BACKGROUND ART

The development and study of new biodegradable, plastic and biocompatible materials for effective organ-specific regeneration with high functional and aesthetic result is the actual problem in modern regenerative medicine and transplantatology. It is obvious that novel materials must meet the requirements of compliance of particular morphology of recipient tissues and promote their functional recovery (Bioartificial organs, 1999; Biocompatibility, 1999; Sudesh et al., 2000; 2004; Biopolymers for Medicinal and Pharmaceutical Applications, 2005).

Currently, the newest area of medical bioengineering concerned with developing of tissue-engineered constructs and bioartificial organs based on biomaterials possessing new functional properties, the so-called histo-equivalent bioplastic materials (HEB), is actively progressing (Shumakov, 1995; Shumakov et al., 2003; Stilman, 2006). A key property of these materials is their ability to biodegradation by natural metabolic pathways with inclusion of intermediate and final products in biochemical cycles without their systemic and local accumulation, as, for example, lactic and glycolic acid are involved in the Krebs cycle. In addition, these materials should not be toxic, and their concentration in the bloodstream should not exceed the maximum permissible limit (Volova T. G., 2003).

The physiological metabolisation of biomaterials, that constitute a frame basis of tissue-engineered constructs, determines the balance of reparative processes without apparent effects of inflammatory reactions and prevents the phenomenon of immune rejection, avoiding the body's response to the foreign body (Shishatskaya E., 2011).

The development of new histo-equivalent bioplastic materials (BM) is based on studying the kinetics of biodegradation and dynamics of its strength properties, as well as on assessing the influence and nature of the regenerative process. The nature and severity of this influence is determined by a combination of physico-chemical properties of the material itself and intensity of responsive physiological and biochemical reactions of a recipient organism.

Therefore, the development of novel biodegradable materials with a maximum degree of biochemical complementarity is based on providing matrixes, consisting of macromolecular complexes, that are exposed to body's self enzyme systems and other lytic agents.

Herewith, the ideal variant of the biodegradable material must meet the following requirements:

1. Macromolecular construct with programmable period of biodegradation in natural metabolic pathways, that is not a source of immuno-inflammatory reactions.
2. Inclusion of intermediate and/or final products of biometabolism of the material in regeneration mechanisms at the phase of the signal chemotaxis of protective cells of the body.
3. Maximum compliance between time period of biodegradation of the material and duration of the reparative process.

Thus, from the point of view of optimal immuno-biochemical compliance, the fulfilment of the above requirements for the development of novel biodegradable materials would provide optimal morphological and functional outcome of organ-specific histogenesis.

Early researches regarding the development of biodegradable materials were focused on natural polymers (collagen, cellulose, and others), and, thereafter, on products of chemical synthesis. Examples of such biodegradable polymers are polyanhydrides, polyesters, polyacryles, poly(methylmethacrylates), polyurethanes. There were several key factors revealed to control the dissolution of the material: hydrophilicity/hydrophobicity, amorphous/crystalline state, molecular weight, presence of heteroatoms (for example, in addition to carbon) (Khlusov I. A., 2007).

Obviously, the most promising are those materials, that form natural monomers upon cleavage. For example, cleavage of polylactides, polyglycolides, polyoxyalkonates and their copolymers provides, respectively, lactic, glycolic, hydroxybutyric acids, which transform in Krebs cycle into water and carbon dioxide, being excreted from a body in natural way.

The prototype of the present invention is nanostructured bioplastic material (Russian Patent No. 2425694 published on Oct. 8, 2011), which includes native form of hyaluronic acid, and is based on a nanostructured matrix representing nanostructured hyaluronic acid obtained by photochemical crosslinking and having a cellular structure in the range from 50 to 100 nm.

Such a structural organization of the macromolecules of hyaluronic acid and collagen provides the biomaterial with elasticity, increased adhesion, drainage properties, transparency.

However, thus obtained macromolecular structure of the bioplastic material is not effective enough in clinical practice.

1. The structure of this material is monophasic, whereby, in the conditions of a wound healing process, it forms uniform coating, thus transforming, into a dry scab (Rakhmatullin R. R. Bioplastic material based on hyaluronic acid: biophysical aspects of the pharmacological properties. // Pharmacy. 2011, No. 4, pp. 37-39). According to clinicians' feedbacks, a homogeneous dry biological scab requires daily bandaging along with mandatory scab wetting, which eventually leads to healing delays and also to scarring accompanied with limitation of functions, e.g., of joints.
2. Complex nanostructured organization of the biomaterial significantly complicates its biometabolization in the wound, i.e. it is not dissolved during healing process and becomes a reason for secondary infection and, as a consequence, complicated course of the wound process. Accordingly, it is necessary to remove the material from the wound during bandaging, however as a dry scab is bounded firmly to the underlying tissue, this procedure is traumatic to the wound and painful for the patient.

3. Monophasic nanostructural organization of the biomaterial does not provide effective drainage of wound fluid and leads to accumulation of the fluid under the biomaterial, therefore it is necessary during bandaging to punch the material using scalpel and to form drainage holes therein (Rakhmatullin R. R., Burlutskaya O. I., Adelshina L. R., Burtseva T. I. Effectiveness of a novel method of repairing skin defect in a patient with congenital epidermolysis bullosa: clinical observation. // Current pediatric issues. 2011, V. 10, No. 2, pp. 190-192). Such manipulations disturb wounds and are painfully tolerated by patients, especially by children.

Thus, the nanostructuring of bioplastic material causes provision of optimal bioengineering properties (adhesion, transparency), but does not provide favorable wound healing and may cause complications.

SUMMARY

The technical result consists in improving the efficiency of wound healing.

The object is solved using histo-equivalent bioplastic material, comprising a base in the form of matrix, for which the native form of hyaluronic acid is used as the material, characterized in that the histo-equivalent bioplastic material contains 1.5% hyaluronic acid solution and 5% peptide complex solution that are mixed to form viscous elastic gel placed in a bed and exposed to ultraviolet photopolymerisation in a laminar flow hood for 5-7 hours, at the following quantitative ratio, ml:

1.5% hyaluronic acid solution—80-90,
5% peptide complex solution—10-20;
wherein the prepared material has perforation and notches.

DETAILED DESCRIPTION

Figure 1:
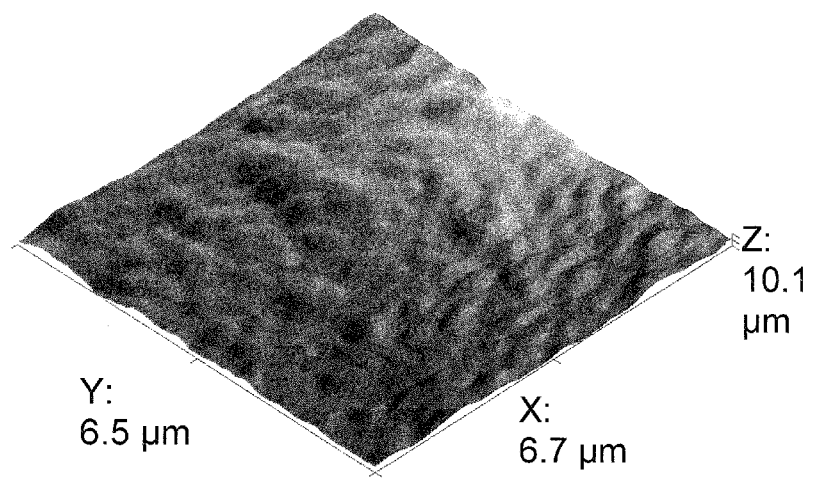
FIG. 1 shows microrelief of the histo-equivalent bioplastic material.
Figure 2:
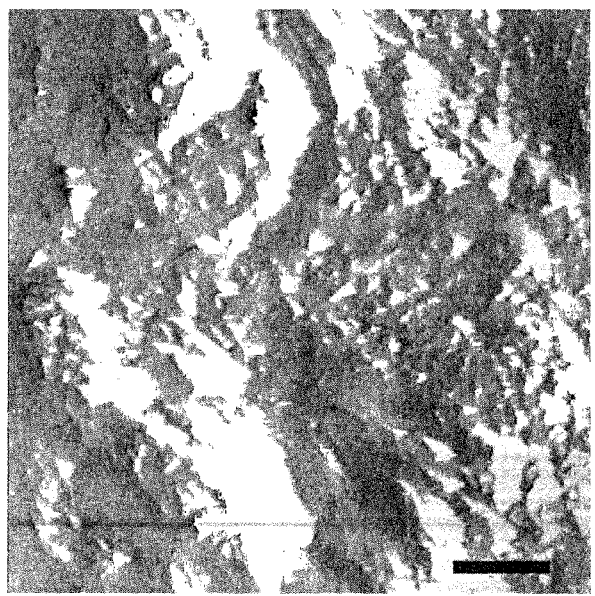
FIG. 2 shows distribution of adhesion forces on the surface of the histo-equivalent bioplastic material.
Figure 3:
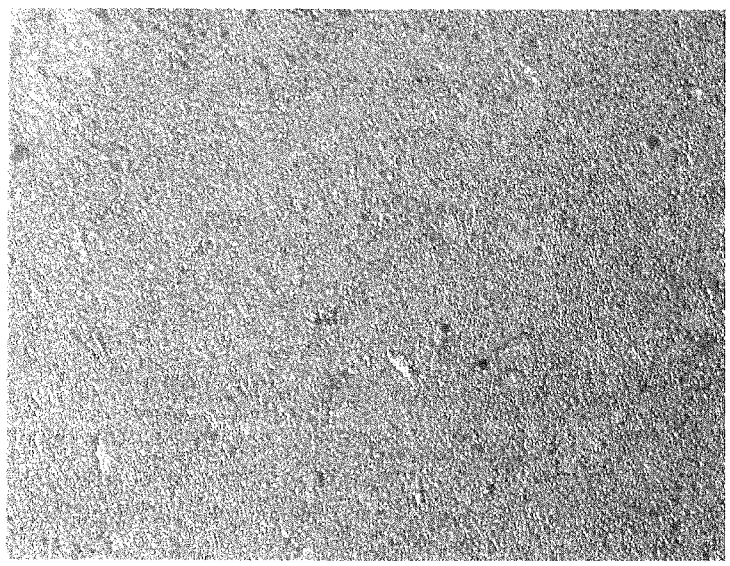
FIG. 3 shows similarity of relief of the biomaterial and human skin pattern.
Figure 4:
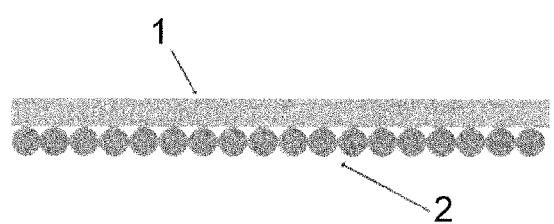
FIG. 4 is a diagram of the biphasic structure of the biomaterial placed in the wound area (1—sheet, 2—hydrocolloid)
Figure 5:
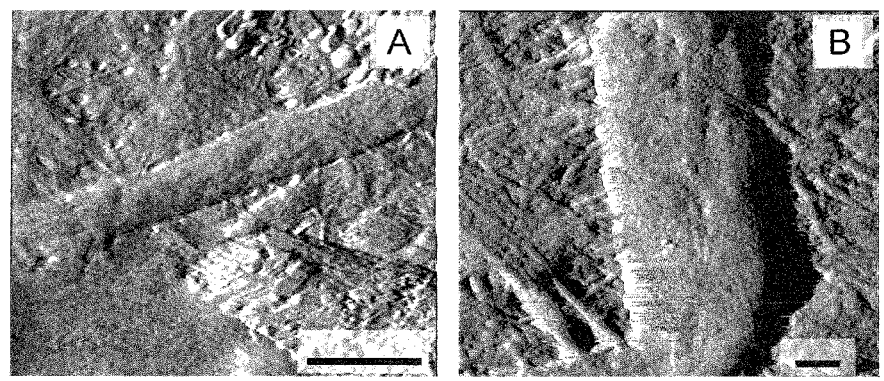
FIG. 5 shows atomic spectrometric image of the biomaterial after cell culturing.
Figure 6:
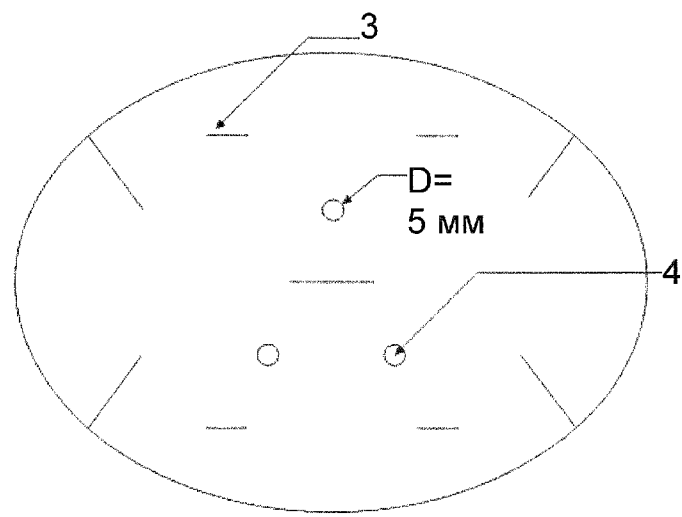
FIG. 6 is an arrangement of notches and holes in the histo-equivalent bioplastic material (3—notches for drainage, 4—holes for autogenous tissue or cells)
Figure 7:
FIG. 7 shows a view of trophic ulcers of the left crus of the patient with diabetes mellitus.
Figure 8:
FIGS. 8 and 9 show steps of bioplastics of the ulcer of the left crus of the patient with diabetes mellitus.
Figure 9:
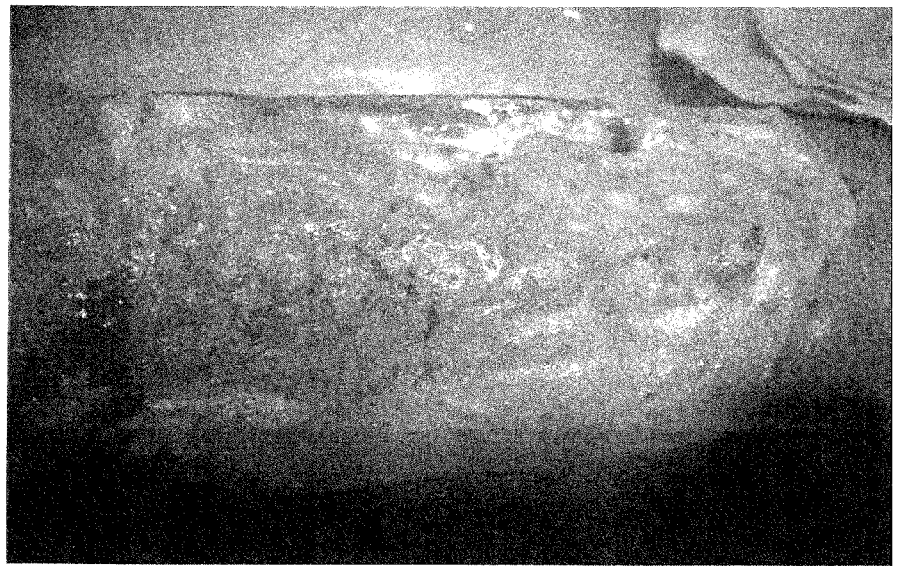
Figure 10:
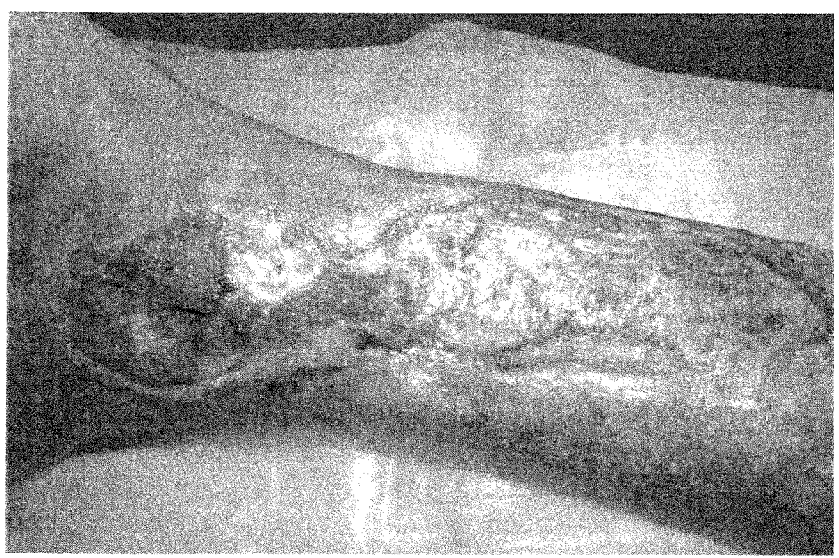
FIGS. 10 and 11 show stages of healing of the ulcer of the left crus of the patient with diabetes mellitus.
Figure 11:

The composition of the peptide complexes comprised in the hydrocolloid of hyaluronic acid is presented in the Table, and it can be seen therefrom that the peptide complexes have different amino acid composition with molecular weight varying from 244 to 459 Da. Among the revealed peptides, aliphatic (leucine, isoleucine, alanine, glycine) and polar uncharged amino acid residues (threonine, proline, histidine, serine), as well as polar charged amino acid residues (arginine, glutamine, asparagine, lysine, arginine) are prevalent. In addition, there are isoleucine dimers and polymeric tripeptides, including peptides containing aromatic amino acid residues (tryptophan) and polar uncharged amino acid residues.

| Examined parameter | Chemical formula | Weight | Delta weight at nanoflow mode | Weight in relative units |
|---|---|---|---|---|
| GlyTrpIle | C19H26N4O4 | 374.19541 | −2.33 | 10.692 |
| IleAspIle | C16H29N3O6 | 359.20564 | 12.97 | 8.674 |
| PheArgPro | C20H30N6O4 | 418.23285 | −0.29 | 9.024 |
| GlnHisHis | C17H24N8O5 | 420.18697 | −5.74 | 17.732 |
| AlaTrpLys | C20H29N5O4 | 403.22195 | −5.76 | 8.934 |
| ProHisTyr | C20H25N5O5 | 415.18557 | −11.10 | 14.407 |
| ThrTrpTrp | C26H29N5O5 | 491.21687 | −12.84 | 9.460 |
| LysPheThr | C19H30N4O5 | 394.22162 | −7.25 | 8.854 |
| LysArgMet | C17H35N7O4S | 433.24712 | 10.73 | 9.102 |
| PheCysMet | C17H25N3O4S2 | 399.12865 | 4.19 | 11.108 |
| IleIle | C12H24N2O3 | 244.17869 | 8.67 | 11.038 |
| AspLysLys | C16H31N5O6 | 389.22743 | 16.59 | 8.863 |
| TrpPro | C16H19N3O3 | 301.14264 | −18.38 | 10.672 |
| GluThr | C9H16N2O6 | 248.10084 | 3.47 | 5.500 |
| Desmosine | C24H40N5O8 | 526.28769 | −15.37 | 9.523 |

It is important that desmosine (amino acid, a lysine derivative) is present in the peptide fraction. Due to its branched structure, that has four amino acid groups, four peptide chains can share one molecule of desmosine. This makes possible to form a two-phase structure of the histo-equivalent bioplastic material.

Biphasic structure of the novel biomaterial allows forming a proper biological scab in wound, which is plate outside, and is in the form of viscous hydrocolloid on the side facing the wound.

In addition, the biphasic structure of the novel biomaterial provides thereof with unique macrorelief pattern due to difference in tension forces. Macrosurface of the histo-equivalent bioplastic biomaterial has unique appearance and looks very similar to human skin dermatoglyphics.

Due to different polarities of the amino acids, the effect of surface tension energy arises, said effect influencing the formation of the unique microrelief.

The images of atomic spectrometric data shows the surface ultrastructure of the preparation as the globular formations of similar morphology having unique relief.

It is known that adhesion of somatic cells more likely occurs on surface of a material having high surface energy (on hydrophilic surface), at the same time the basic cellular processes (growth, differentiation, migration) are influenced to a greater extent by geometric and dimensional features of a substrate' relief (Hertz H. Uber die Beruhrung Fester Elastischer Korper (On the contact of elastic solids) // J. Reine Angew. 2011, No. 292, pp. 156-171).

By assessing the hydrophilic/hydrophobic properties of the biomaterial according to the invention using the method for fixation of the contact angle of water, which amounted to 83°, the authors calculated the work of adhesion on this basis, which, taking into account the roughness coefficient, was equal to 99.88 mN/m, that characterizes the surface of the novel material as moderately wettable.

Additional imaging of the surface of the biopolymer in the mode for registration the adhesion forces allowed to localize areas having enhanced adhesion.

The surface energy of adhesion forces is a fundamental feature of bioplastic materials allowing to evaluate effective migration of cells thereon during regeneration. It was established that the presence of local areas exerting different adhesion ensures directional cell taxis and homogeneous distribution over the entire surface (Hallab N. J., Bundy K. J., O'Connor K. et al. Evaluation of metallic and polymeric biomaterial surface energy and surface roughness characteristics for directed cell adhesion // Tissue engineering. 2001, V. 7, No. 1, pp. 55-71).

As thermodynamic work of water on the surface of histo-equivalent bioplastic material is evaluated by limiting wetting angle, the determined adhesion forces values characterize its biphasic biomaterial having hydrophilic/hydrophobic properties. This is due to the presence of heteropolar substances (amino acids of the peptide complex) spatially distributed in the structure of hydrocolloid of hyaluronic acid that acts as matrix base of the material.

This was proved by direct visualization of the biomaterial's surface in the mode of adhesion-contact atomic force microscopy. The results obtained indicate the presence of areas, which are significant in relation to the visualized area, showing adhesive properties on the biomaterial surface.

In turn, cultivation of mesenchymal stromal stem cells using the histo-equivalent bioplastic material as a substrate and subsequent atomic force microscopy of the surface allowed to detect the presence of oblong shaped cells having width of 3.7 μm. Subsequent more detailed study revealed the presence of intertwined fibrillar fibers on the cell's surface. The similar nature of their location is an evidence of existence of cultivated mesenchymal stem cell migration, whereby they actively interact with the surface of the substrate infiltrating into the underlying matrix.

Thus, the presence of peptide complex provides the organization of two-phase structure of the biomaterial, which is a basis for the formation of proper biological scab in the wound (a plate on the outer surface, hydrocolloid inside).

The histo-equivalent bioplastic material has through microperforations for effective drainage of wound fluid.

The maximum morphological similarity of the structure and appearance between the biomaterial and epithelium tissues (skin) gives reasons for introduction the term "Histo-equivalent bioplastic material" in the title of the invention.

The histo-equivalent bioplastic material is prepared as follows.

As raw materials, hyaluronic acid in native form having fibrous nanostructure capable of forming elastic plate and the peptide complex are used. The native form of hyaluronic acid provides optimal conditions for migration and proliferation of cells, the source of which are pieces of viable tissue, placed in the area of microperforations (a kind of cellular cells) of the histo-equivalent bioplastic material.

Prepared are the 1.5% hyaluronic acid solution and the 5% peptide complex solution, at room temperature. Then they are mixed to form viscous elastic gel.

Then the viscous elastic gel is placed in a bed-mould and subjected to ultraviolet photopolymerization in specially designed laminar flow hood.

For that purpose, special microclimate (temperature is 0-3° C., humidity is ~50-55%, with ventilation at air flow rate of 0.50 m/s) is created in the laminar flow hood. The mixture is then subjected to ultraviolet irradiation for 5-7 hours. The prepared material is transferred to apparatus for perforating and packaging.

As a result, elastic plate of whitish color is formed in the moulds which is very similar to the dermatoglyphics of human skin pattern.

The plate is cut into oval (the major diameter is 15 cm, the minor one is 11 cm), the area of oval plate corresponds to the average area of an adult's palm. In medicine, it is considered that an adult's palm constitutes about 5% of the body's surface; for example, the area of burns is estimated in such a way.

Then round holes are punched in the plate with hole puncher, and then notches are cut mechanically with a special knife. Uniformly distributed notches are required for drainage of wound exudate and for improved adhesion between the biomaterial and the underlying tissue. The round holes 3 mm in diameter function as planting holes for epithelial tissues. These tissues are patient's self-tissues, which are dissected from edges of the wound during its surgical treatment. Further they serve as sources of cells for effective epithelization (healing) of the wound.

As a result of clinical use in patients with defects of epithelium tissues, it was found, that the histo-equivalent bioplastic material forms a proper biological scab and promotes rapid wound healing.

It is important to note, that the histo-equivalent bioplastic material is proved to be effective in patients who can't receive any help from conventional therapy.

Clinical Example

Woman Patient A., 59 years old, lives in Kuvandyk, admitted in the $4^{th}$ surgical unit of Orenburg regional clinical hospital at railway station Orenburg of JSC "RZD" on Dec. 16, 2011 with the diagnosis: giant circular necrotic trophic ulcer of the left crus; severe diabetes mellitus type 2; allergic dermatitis of legs; anemia.

The Patient suffers from the disease for 1 year after ulceration resulted from necrotizing erysipelas. The size of the defect—circular band of 8 to 10 cm width from lower third to middle third of crus with elements of fascia and tendons in the wound bed. All treatment methods that were used previously, including bandaging with antiseptics, ointments and various wound coverings, did not lead to any effect and were extremely painfully tolerated by the Patient.

Upon admission, surgical debridement of wound was performed, necrotic areas were excised, rounded pieces of viable skin tissue of 0.5 to 1 mm in size were obtained. Then, the histo-equivalent bioplastic material having microperforations of 3 mm in diameter and notches in its structure was applied on the prepared wound. After the biomaterial adhered to the wound and transformed into elastic plate, the pieces of viable tissues of the Patient taken out from saline were put in the perforations of the biomaterial. After all microperforations were filled with the pieces of tissue, sterile cloth and bandage were applied thereon.

The long course of complex conservative treatment with correction of comorbidity were performed. Observed was the formation of the two-phase structure of the biomaterial in the wound area: the external side is the biological scab, and the internal one is hydrocolloid.

After cleaning the wound, flat granulating circular defect with marginal epithelization was formed.

When using the histo-equivalent bioplastic material, it was found, that it has the most powerful stimulating effect on fibroblasts by promoting CD44 receptors to synthesize self hyaluronic acid, collagen type III and elastin, whereby preventing formation of hypertrophic scars.

As a result of the treatment with the claimed biomaterial, it was noted that all patients reported that the pain disappeared upon 2-3 hours after applying. Subsequently it was observed that there was no phenomenon of contractural changes in the wound area, and there was full regeneration of the skin. It should be noted, that the use of this biomaterial prevented inflammatory response (sepsis) and the formation of hypertrophic scars during the rehabilitation period. None case of allergic and/or inflammatory reaction in patients was observed.

Thus, in comparison with the prototype, the studies show that the histo-equivalent bioplastic material is capable to form a proper biological scab and to stimulate the healing of wounds with good aesthetic results without scarring, and also has high biocompatibility to epithelium tissues in human body.

Novelty of the claimed histo-equivalent bioplastic material is an original composition of peptide complex that includes heteropolar amino acids. The presence of this peptide complex provides for the formation of the two-phase structure of the biomaterial, which is the basis for the formation of a proper biological scab in a wound (plate is outside, hydrocolloid is inside).

The histo-equivalent bioplastic material has through microperforations for effective drainage of wound fluid. A distinctive feature of this histo-equivalent bioplastic material is its ability to form a two-phase wound covering and thus to form a proper biological scab, to drain the wound effectively, that ultimately provides optimal regeneration of the defect of epithelium tissues without scarring and deformation. In addition, the biomaterial has a special planting holes for the patient's self tissue, of which the germ areas for wound healing are formed.

The embodiments of the invention described above are provided by way of example only. The skilled person will be aware of many modifications, changes and substitutions that could be made without departing from the scope of the present invention. The claim of the present invention is intended to cover all such modifications, changes and substitutions as fall within the spirit and scope of the invention.

We claim:

1. A biphasic histo-equivalent bioplastic material in the form of an elastic plate, comprising hyaluronic acid and a peptide complex wherein the peptide complex comprises desmosine, the bioplastic material being formed by ultraviolet polymerization of a mixture of 80-90 volume % of a 1.5% hyaluronic acid solution and 10-20 volume % of a 5% peptide complex solution, whereby a biphasic polymer material is formed.

2. The histo-equivalent bioplastic material of claim 1 which consists of hyaluronic acid and the peptide complex.

3. The histo-equivalent bioplastic material of claim 1 in the form of an elastic plate which has perforations and notches therein.

4. A process for preparing a biphasic histo-equivalent bioplastic material comprising hyaluronic acid and a peptide complex, the process comprising mixing 80-90 volume % of a 1.5% hyaluronic acid solution and 10-20 volume % of a 5% peptide complex solution to form a viscous elastic gel, placing the gel in a mold, and exposing the gel to ultraviolet photopolymerization for 5 to 7 hours.

5. The process of claim 4 wherein the peptide complex comprises desmosine.

* * * * *